(12) United States Patent
McNaughton-Smith et al.

(10) Patent No.: US 6,288,122 B1
(45) Date of Patent: Sep. 11, 2001

(54) GARDOS CHANNEL ANTAGONISTS

(75) Inventors: Grant Andrew McNaughton-Smith, Morrisville; Gregory Cooksey Rigdon; Jonathan Walter Stocker, both of Durham, all of NC (US)

(73) Assignee: Icagen, Inc., Durham, NC (US)

( * ) Notice: Subject to any disclaimer, the term of this patent is extended or adjusted under 35 U.S.C. 154(b) by 0 days.

(21) Appl. No.: 09/386,601

(22) Filed: Aug. 31, 1999

Related U.S. Application Data
(60) Provisional application No. 60/135,511, filed on Feb. 23, 1999.

(51) Int. Cl.$^7$ ..................... A61K 31/165; C07C 233/65
(52) U.S. Cl. ......................... 514/617; 564/181; 564/182
(58) Field of Search ............... 514/617; 564/181, 564/182

(56) References Cited

U.S. PATENT DOCUMENTS
5,273,992  12/1993  Brugnara et al. .

FOREIGN PATENT DOCUMENTS
WO 97/34589  9/1997  (WO) ............. A61K/31/14

OTHER PUBLICATIONS
Bartroli, et al., *Arzneim.–Forsch./Drug Res.*, 42(I)(6):832–835 (1992).
Benzaquen, et al., *Nature Medicine*, 1(6):534–540 (1995).
Brugnara, et al., *J. Biol. Chem.*, 268(12):8760–8768 (1993).
Brugnara, et al., *J. Clin. Invest.*, 92:520–526 (1993).
Brugnara, et al., *J. Clin. Invest.*, 97(5):1227–1234 (1996).
Brugnara, et al., *JPET*, 273:266–272 (1995).
Conte, et al., *Arzneim.–Forsch./Drug Res.*, 42(I)(6):854–858 (1992).
De Franceschi, et al., *J. Clin. Invest.*, 93:1670–1676 (1994).
Rodriguez, et al., *J. Biochem. Toxicol.*, 11(3):127–131 (1996).
Rodriguez, et al., *Toxicology*, 96:83–92 (1995).
Trudel et al., *EMBO J.*, 10(11):3157–3165 (1991).
Von K. H. Büchel, et al., *Arzneim.–Forsch./Drug Res.*, 22(8):1260–1272 (1972) (English summary—pp. 1271–1272).

*Primary Examiner*—Shailendra Kumar
(74) *Attorney, Agent, or Firm*—Townsend and Townsend and Crew LLP

(57) ABSTRACT

Novel inhibitors of potassium flux are disclosed. The inhibitors show surprising resistance to degradation in biological media and enhanced in vivo half-lives relative to non-fluorine substituted homologues. Methods for the use of these compounds include treating sickle cell disease, preventing erythrocyte dehydration and inhibiting potassium flux.

25 Claims, 1 Drawing Sheet

GARDOS CHANNEL ANTAGONISTS

CROSS REFERENCE TO RELATED APPLICATIONS

This application claims priority to U.S. Provisional Application Serial No. 60/135,511, filed on Feb. 23, 1999, the disclosure of which is incorporated herein by reference for all purposes.

FIELD OF THE INVENTION

The present invention relates to organic compounds that are specific, potent and safe inhibitors of the $Ca^{2+}$-activated potassium channel (Gardos channel) of erythrocytes. More particularly, the invention relates to fluorine substituted triarylmethane-based inhibitors that exhibit remarkably enhanced resistance to degradation in in vitro biological media and exhibit extended in vivo half-lives relative to their non-fluorinated homologues.

BACKGROUND OF THE INVENTION

Sickle cell disease has been recognized within West Africa for several centuries. Sickle cell anemia and the existence of sickle hemoglobin (Hb S) was the first genetic disease to be understood at the molecular level. It is recognized today as the morphological and clinical result of a glycine to valine substitution at the No. 6 position of the beta globin chain (Ingram, Nature 178: 792–794 (1956)). The origin of the amino acid change and of the disease state is the consequence of a single nucleotide substitution (Marotta et al., J. Biol. Chem. 252:5040–5053 (1977)).

The major source of morbidity and mortality of patients suffering from sickle cell disease is vascular occlusion caused by the sickled cells, which causes repeated episodes of pain in both acute and chronic form and also causes ongoing organ damage with the passage of time. It has long been recognized and accepted that the deformation and distortion of sickle cell erythrocytes upon complete deoxygenation is caused by polymerization and intracellular gelation of sickle hemoglobin, hemoglobin S (Hb S). The phenomenon is well reviewed and discussed by Eaton et al., Blood 70:1245 (1987). The intracellular gelatin and polymerization of Hb S can occur at any time during an erythrocyte's journey through the vasculature. Thus, erythrocytes in patients with sickle cell disease containing no polymerized hemoglobin S may pass through the microcirculation and return to the lungs without sickling, may sickle in the veins or may sickle in the capillaries.

The probability of each of these events is determined by the delay time for intracellular gelation relative to the appropriate capillary transit time (Eaton, et al., Blood 47: 621(1976)). In turn, the delay time is dependent upon the oxygenation state of the hemoglobin, with deoxygenation shortening the delay time. If it is thermodynamically impossible for intracellular gelation to take place, or if the delay time at venous oxygen pressures is longer than about 15 seconds, cell sickling will not occur. If the delay time is between about 1 and 15 seconds, the red cell will likely sickle in the veins. If the delay time is less than about 1 second, red cells will sickle within the capillaries.

For red cells that sickle within the capillaries, a number of consequent events are possible. These range from no effect on transit time, to transient occlusion of the capillary, to a more permanent blockage that may ultimately result in ischemia or infarction of the surrounding cells, and in the subsequent destruction of the red cell.

Normal erythrocytes are comprised of approximately 70% water. Water crosses a normal erythrocyte membrane in milliseconds. Loss of cell water causes an exponential increase in cytoplasmic viscosity as the mean cell hemoglobin concentration (MCHC) rises above about 32 g/dl. Since cytoplasmic viscosity is a major determinate of erythrocyte deformability and sickling, the dehydration of the erythrocyte has substantial rheological and pathological consequences. Regulation of erythrocyte dehydration is recognized as an important therapeutic approach for treating sickle cell disease. Since cell water follows any osmotic change in intracellular ion concentration, maintaining the red cell's potassium concentration is of particular importance (Stuart et al., Brit J. Haematol. 69:1–4 (1988)).

Many approaches to therapeutically treating dehydrated sickle cells (thus decreasing polymerization of hemoglobin S by lowering the osmolality of plasma) have been tried with limited success, including the following approaches: intravenous infusion of distilled water (Gye et al., Am. J. Med. Sci. 266: 267–277(1973)); administration of the antidiuretic hormone vasopressin together with a high fluid intake and salt restriction (Rosa et al., M. Eng. J. Med. 303:1138–1143 (1980)); Charache et al., Blood 58: 892–896 (1981)); the use of monensin to increase the cation content of the sickle cell (Clark et al., J. Clin. Invest. 70:1074–1080 (1982)); Fahim et al., Life Sciences 29:1959–1966 (1981)); intravenous administration of cetiedil citrate (Benjamin et al., Blood 67: 1442–1447 (1986)); Berkowitz et al., Am. J. Hematol. 17: 217–223 (1984)); Stuart et al., J. Clin. Pathol. 40:1182–1186 (1987)); and the use of oxpentifylline (Stuart et al., supra).

Another approach towards therapeutically treating dehydrated sickle cells involves altering erythrocyte potassium flux by targeting a calcium-dependent potassium channel (Ishi et al., Proc. Natl. Acad. Sci. 94(21): 11651–6 (1997)). This calcium activated potassium channel is also referred to as the Gardos channel (Brugnara et al, J. Clin. Invest. 92: 520–526 (1993)). Recently, a cloned human intermediate conductance calcium activated potassium channel, hIK1, was shown to be substantially similar to the Gardos channel in terms of both its biophysical and pharmacological properties (Ishi, supra).

Methods that have been used to inhibit the Gardos channel include the administration to erythrocytes of imidazole, nitroimidazole and triazole antimycotic agents such as clotrimazole (U.S. Pat. No. 5,273,992 to Brugnara et al.). Clotrimazole, an imidazole-containing antimycotic agent, has been shown to be a specific, potent inhibitor of the Gardos channel of normal and sickle erythrocytes, and prevents $Ca^{2+}$-dependent dehydration of sickle cells both in vitro and in vivo (Brugnara, supra; De Franceschi et al., J. Clin. Invest. 93: 1670–1676 (1994)). When combined with a compound which stabilizes the oxyconformation of Hb S, clotrimazole induces an additive reduction in the clogging rate of a micropore filter and may attenuate the formation of irreversibly sickled cells (Stuart et al., J. Haematol. 86:820–823 (1994)). Other compounds that contain a heteroaryl imidazole-like moiety believed to be useful in reducing sickle erythrocyte dehydration via Gardos channel inhibition include miconazole, econazole, butoconazole, oxiconazole and sulconazole. Although these compounds have been demonstrated to be effective at reducing sickle cell dehydration, other imidazole compounds have been found incapable of inhibiting the Gardos channel and preventing loss of potassium.

Since sickle cell anemia is a chronic disease, agents designed for treating it will ideally exhibit certain characteristics that are less essential in drugs for treating resolvable illnesses (e.g., fungal infections). A clinically useful Gardos channel inhibitor will exhibit extremely low toxicity over a prolonged course of administration, will have an excellent bioavailability, will be highly specific for the Gardos channel and will be potent in its interactions with this channel.

Although clotrimazole and certain related compounds have been shown to inhibit the Gardos channel and prevent loss of potassium, these compounds are less than ideal clinical agents for the treatment of sickle cell anemia. Of primary concern is the fact that prolonged administration of imidazole antimycotics has been demonstrated to result in hepatotoxicity (see, for example, Rodriguez el al., *Toxicology* 6: 83–92 (1995); Findor et al., *Medicina* 58: 277–81 (1998); and Rodriguez et al., *J. Biochem. Toxicol.* 11: 127–31 (1996)). The trend towards toxicity of an agent must be balanced with other characteristics such as its bioavailability, target selectivity and potency.

Presently known Gardos channel inhibitors have low in vivo half lives and low bioavailabilities. These deficiencies are of particular concern in conjunction with these drugs, as they must be regularly administered over a significant portion of a person's lifetime. With such drugs, patient compliance with the dosage regimen is crucial, and the simpler the regimen, the more likely a patient will comply with the regimen. Gardos channel inhibitors having low bioavailabilities must be frequently administered, raising the risk of missed doses and consequent plasma drug levels inadequate to prevent the dehydration of erythrocytes. In addition to frequent dosing, agents having low bioavailabilities must generally be administered in higher dosages than analogous agents with better bioavailabilities. At higher dosages, undesirable side effects and toxicity become a very real concern.

In addition to their low bioavailability, known Gardos channel inhibitors such as clotrimazole also have relatively low potency in their interaction with the Gardos channel. The low potency of the compounds is exacerbated by their low bioavailability and rapid systemic clearance. A further shortcoming of many known Gardos channel inhibitors is the non-specific nature of their interactions with calcium activated potassium channels: these agents readily interact with calcium activated potassium channels other than the Gardos channel. Taken together, the low potency, low specificity and low bioavailability of known Gardos channel inhibitors mandate higher and more frequent dosing, thereby increasing the risk of undesirable side effects and toxicity.

In view of the above-described shortcomings of currently known Gardos channel inhibitors a substantial advance in the treatment of sickle cell anemia is expected from the discovery of Gardos channel inhibitors that do not contain imidazole as a structural component, are appreciably bioavailable, slowly metabolized and excreted and are both potent and specific in their interactions with the Gardos channel. Quite surprisingly, the present invention provides Gardos channel inhibitors having these characteristics.

SUMMARY OF THE INVENTION

Figure 1:
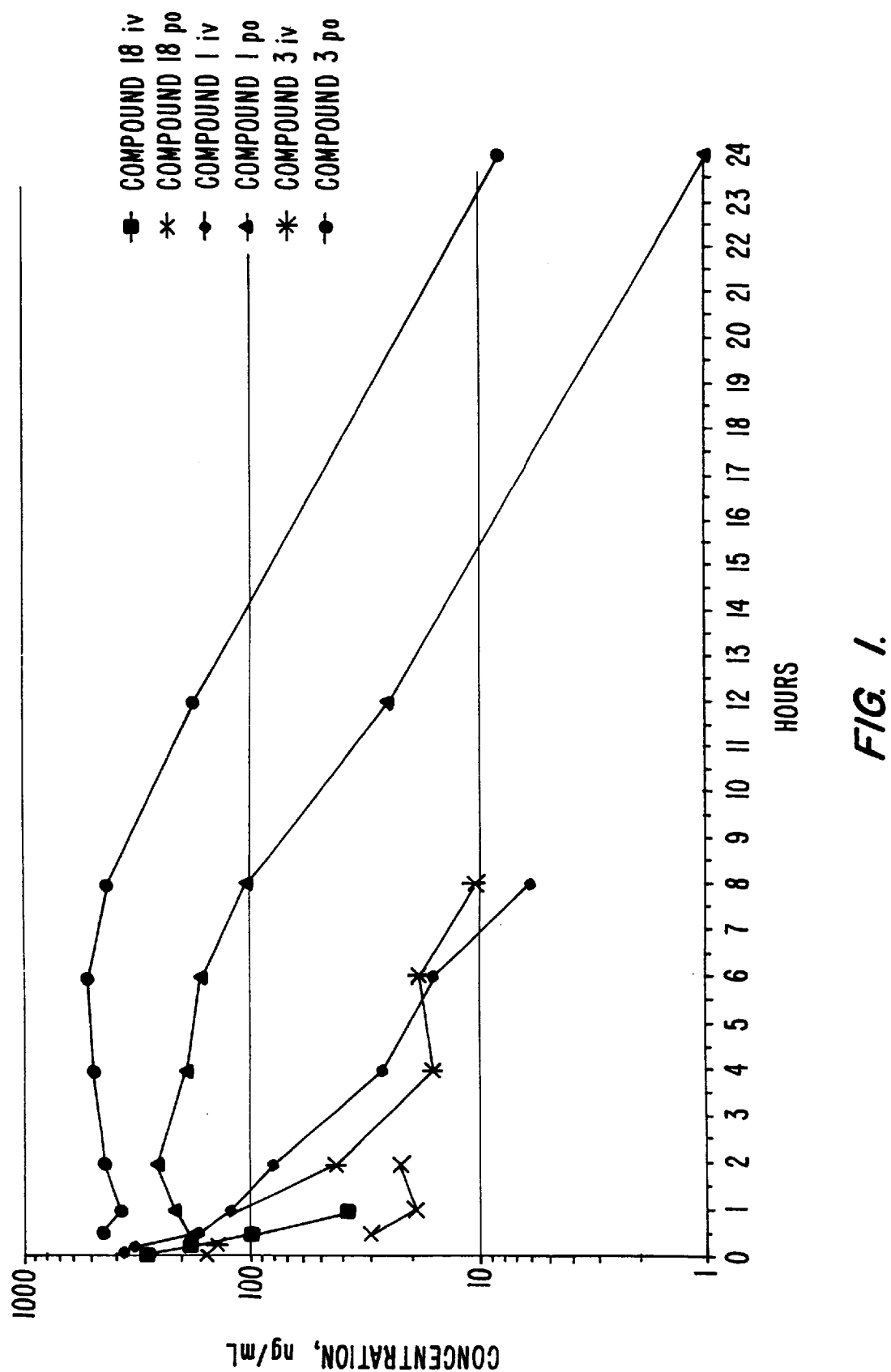
FIG. 1 is a plot of the mean plasma concentration versus time for compounds 1 (i.v. (♦), oral (▲)), 3 (i.v. (*), oral (●) and 18 (i.v. (■), oral (X)). The dosages were, i.v. (1 mg/kg) and oral (10 mg/kg).

Reducing sickle erythrocyte dehydration via blockade of the Gardos channel is a powerful therapeutic approach towards the treatment and/or prevention of sickle cell disease. Compounds capable of inhibiting the Gardos channel as a means of reducing sickle cell dehydration are highly desirable, and are an object of the present invention. Although of demonstrable efficacy, the imidazole-based Gardos channel inhibitors that have been explored to date are hampered by several shortcomings including a well-documented potential for hepatotoxicity. This toxicity is exacerbated by the inhibitors' low potencies, non-specific interactions with calcium activated potassium channels other than the Gardos channel and low bioavailabilities, each of which motivate for the administration of higher and more frequent dosages of the inhibitors.

In contrast to these known agents, a pharmaceutically usefull second-generation Gardos channel inhibitor will exhibit prolonged stability in a biological milieu and potency and selectivity for the Gardos channel. An ideal agent is less than 60% degraded after a two hour incubation in a biological milieu (e.g., a microsome preparation) and has an $IC_{50}$ towards the Gardos channel of not more than 30 nM. Moreover, these agents are at least 100-fold more selective for the Gardos channel than for other potassium channels, such as $I_{Ks}$.

It has now been discovered that triphenylacetamide-based inhibitors of the Gardos channel, wherein one or more phenyl groups is substituted with one or more fluorine atoms or fluorine-containing moieties, have in vivo half-lives and in vitro metabolic stabilities that are enhanced to a surprising degree relative to both clotrimazole and analogous non-fluorinated triphenylacetamides. For example, clotrimazole (19) is 94.2% degraded after incubating two hours in a liver microsome preparation and a non-fluorinated triphenylmethylacetamide (20) is 87% degraded after 2 hours. In marked contrast, representative difluorinated compounds of the invention 3 and 5 are, respectively, only 24% and 29% degraded after a similar incubation.

Although studies on fluorinated triphenylimidazole antimycotics demonstrated that these fluorinated agents were less rapidly metabolized than their chlorinated analogues, these agents were also less pharmacologically active than analogous chlorinated derivatives (see, Conte et al., *Arneim-Forsch./Drug Res.* 42: 854–858 (1992); and Bartoli, et al., *Arneim-Forsch./Drug Res.* 42: 832–835 (1992)). Surprisingly, however, quite the opposite trend is observed for the compounds of the invention: the fluorinated compounds are not only more potent, but also more selective inhibitors of the Gardos channel than clotrimazole. For example, compounds 3 and 5 are approximately 8- and 10-fold more potent than clotrimazole towards the Gardos channel. Moreover, compounds 3 and 5 are approximately 16- and 17-fold more selective for the Gardos channel over other potassium ion channels (e.g., $I_{Ks}$) than clotrimazole.

Thus, in a first aspect, the present invention provides a compound having a structure according to Formula (I):

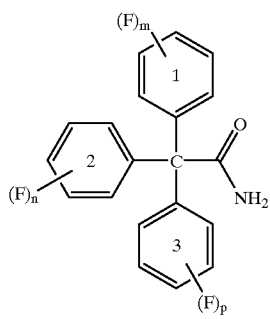

(I)

wherein,
  m, n and p are independently selected from 0 and 1 and at least one of m, n and p is 1;
  when m, n and p are all 1, the fluoro substituents at ring 1 and at ring 2 are located at a position independently selected from ortho to the acetamide substituent, meta to the acetamide substituent and para to the acetamide substituent, and the substituent at ring 3 is at a position selected from ortho to the acetamide substituent para to the acctamide substituent; and
  when p is 0, and m is 1 and n is 1, the fluoro substituent at ring 1 is para to the acetamide substituent, and the substituent at ring 2 is located at a position selected from ortho to the acetamide substituent and para to the acetamide substituent.

In a second aspect, the present invention provides a pharmaceutical composition comprising a compound according to Formula (I) in admixture with a pharmaceutically acceptable excipient. Such a preparation can be administered in methods of the invention.

Controlling diseases (e.g., sickle cell disease) via altering cellular ionic fluxes of cells affected by a disease is a powerful therapeutic approach. Moreover, basic understanding of the role of cellular ionic fluxes in both disease processes and normal physiology promises to provide new therapeutic modalities, regimens and agents. Compounds that alter cellular ion fluxes, particularly those that inhibit potassium flux, are highly desirable as both drugs and as probes for elucidating the basic mechanisms underlying these ion fluxes. Similarly, methods utilizing these compounds in basic research and in therapeutic applications are valuable tools in the arsenal of both the researcher and clinician. Therefore such compounds and methods are also an object of the present invention.

Thus, in a third aspect, the present invention provides a method of inhibiting potassium flux of a cell. The method comprises contacting a cell with an amount of a compound according to Formula (I) effective to inhibit the potassium flux.

An important therapeutic pathway for treatment of sickle cell disease is preventing or retarding the dehydration of erythrocytes by manipulating the cellular ion fluxes of erythrocytes. Thus, in another aspect, the invention provides a method for reducing erythrocyte dehydration. The method comprises contacting an erythrocyte with an amount of a compound according to Formula (I) effective to reduce erythrocyte dehydration.

In a fifth aspect, the invention provides a method of treating or preventing sickle cell disease. The method comprises administering to a subject suffering sickle cell disease a therapeutically effective amount of a compound having a structure according to Formula (I).

The compounds of the invention represent a novel class of inhibitors of calcium activated potassium flux that display excellent resistance towards metabolic degradation and both a selectivity and a potency towards the Gardos channel that is enhanced relative to their non-fluorinated analogues. Thus, in a sixth aspect, the present invention provides a method for enhancing the resistance to degradation in a biological medium of a potassium channel inhibitor, comprising a triphenylmethyl moiety.

These and other objects and advantages of the present invention will be apparent from the detailed description and examples that follow.

DETAILED DESCRIPTION OF THE INVENTION AND THE PREFERRED EMBODIMENTS

Abbreviations and Definitions

"MCHC," is the "mean corpuscular hemoglobin concentration."

"SAD-1" is a transgenic mouse model of sickle cell disease as described by Trudel et. al., *EMBO J.*, 10(11): 3157–3165 (1991).

"Biological medium," as used herein refers to both in vitro and in vivo biological milieus. Exemplary in vitro "biological media" include, but are not limited to, cell culture, tissue culture, homogenatcs, plasma and blood. In vivo applications are generally performed in mammals, preferably humans.

"Fluoroalkyl" refers to a subclass of"substituted alkyl" encompassing alkyl or substituted alkyl groups that are either partially fluorinated or per-fluorinated. The fluorine substitution can be the only substitution of the alkyl moiety or it can be in substantially any combination with any other substituent or group of substituents.

Introduction

As discussed in the above, blockade of sickle dehydration via inhibition of the Gardos channel is a powerful therapeutic approach for the treatment and/or prevention of sickle cell disease. In vitro studies have shown that clotrimazole, an imidazole-containing antimycotic agent, blocks $Ca^{2+}$-activated $K^+$ flux and cell dehydration in sickle erythrocytes (Brugnara et al., *J. Clin. Invest.* 92: 520–526 (1993)). Studies in a transgenic mouse model for sickle cell disease, SAD-1 mouse (Trudel et al., *EMBO J.* 11: 3157–3165 (1991)), show that oral administration of clotrimazole leads to inhibition of the red cell Gardos channel, increased red cell $K^+$ content, a decreased mean corpuscular hemoglobin concentration (MCHC) and decreased cell density (De Franceschi et al., *J. Clin. Invest.* 93: 1670–1676 (1994)). Moreover, therapy with oral lotrimazole induces inhibition of the Gardos channel and reduces erythrocyte ehydration in patients with sickle cell disease (Brugnara et al., *J. Clin. Invest.* 97: 1227–1234 (1996)). Other antimycotic agents, which inhibit the Gardos channel in vitro, include miconazole, econazole butoconazole, oxiconazole and sulconazole (U.S. Pat. No. 5,273,992 to Brugnara et al.). All of these compounds contain an imidazole-like ring. i.e., a heteroaryl ring containing two or more nitrogens.

Although of demonstrable efficacy, the imidazole-based Gardos channel inhibitors that have been explored to date are hampered by several shortcomings including a well-documented potential for hepatotoxicity. This toxicity is exacerbated by the inhibitors' low potencies, non-specific interactions with potassium channels other than the Gardos channel and low bioavailabilities, each of which motivate for the administration of higher and more frequent dosages of the inhibitors.

To provide superior pharmaceutical agents capable of inhibiting the Gardos channel, three pharmacological criteria must be met. First, the compounds must be stable in a biological milieu, such that at least 40% of the compound remains intact after two hours in this milieu. Moreover, the compounds must be potent inhibitors of the Gardos channel, having an $IC_{50}$ towards this channel of less than or equal to 30 nM. In addition to their potency towards the Gardos channel, the compounds must also be selective in their interaction with this channel. The compounds must have a selectivity as measured by an $IC_{50}$ ratio ($IK_{Ks}$/Gardos) of greater than or equal to 80.

Compounds

In a first aspect, the present invention provides a compound having a structure according to Formula (I):

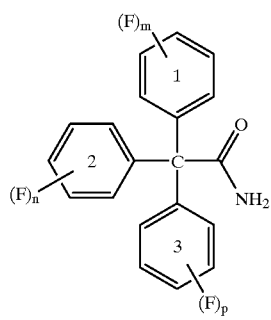

(I)

wherein, m, n and p are independently selected from 0 and 1 and at least one of m, n and p is 1;

when m, n and p are all 1, the fluoro substituents at ring 1 and at ring 2 are located at a position independently selected from ortho to the acetamide substituent, meta to the acetamide substituent and para to the acetamide substituent, and the substituent at ring 3 is at a position selected from ortho to the acetamide substituent para to the acetamide substituent; and when p is 0, and m is 1 and n is 1, the fluoro substituent at ring 1 is para to the acetamide substituent, and the substituent at ring 2 is located at a position selected from ortho to the acetamide substituent and para to the acetamide substituent.

In a presently preferred embodiment, the compounds of the invention have a structure according to Formula (II):

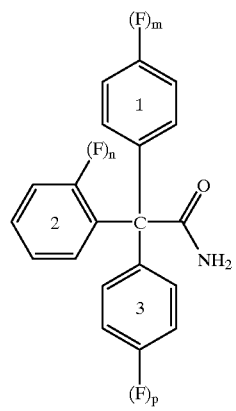

(II)

wherein, m, n and p are independently selected from 0 and 1, and at least one of m, n and p is 1.

Compounds according to this structure are displayed in Table 1 and include compounds 1–5.

In another preferred embodiment, the compounds of the invention have a structure according to Formula III:

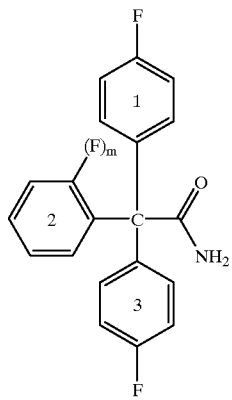

(III)

wherein m is either 0 or 1.

Compounds according to Formula III are displayed in Table 1 and include compounds 3 and 5.

Compounds that are structurally closely related to compounds of the invention are also displayed in Table 1. The compounds which are structurally related to the compounds of the invention serve as a "baseline" for assessing the advantages and unexpected properties and benefits of the fluorinated compounds of the invention.

TABLE 1

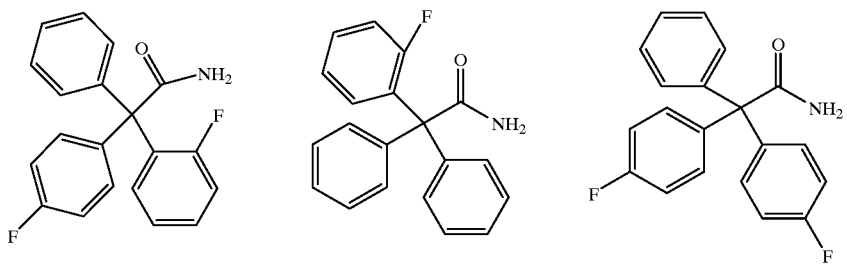

TABLE 1-continued
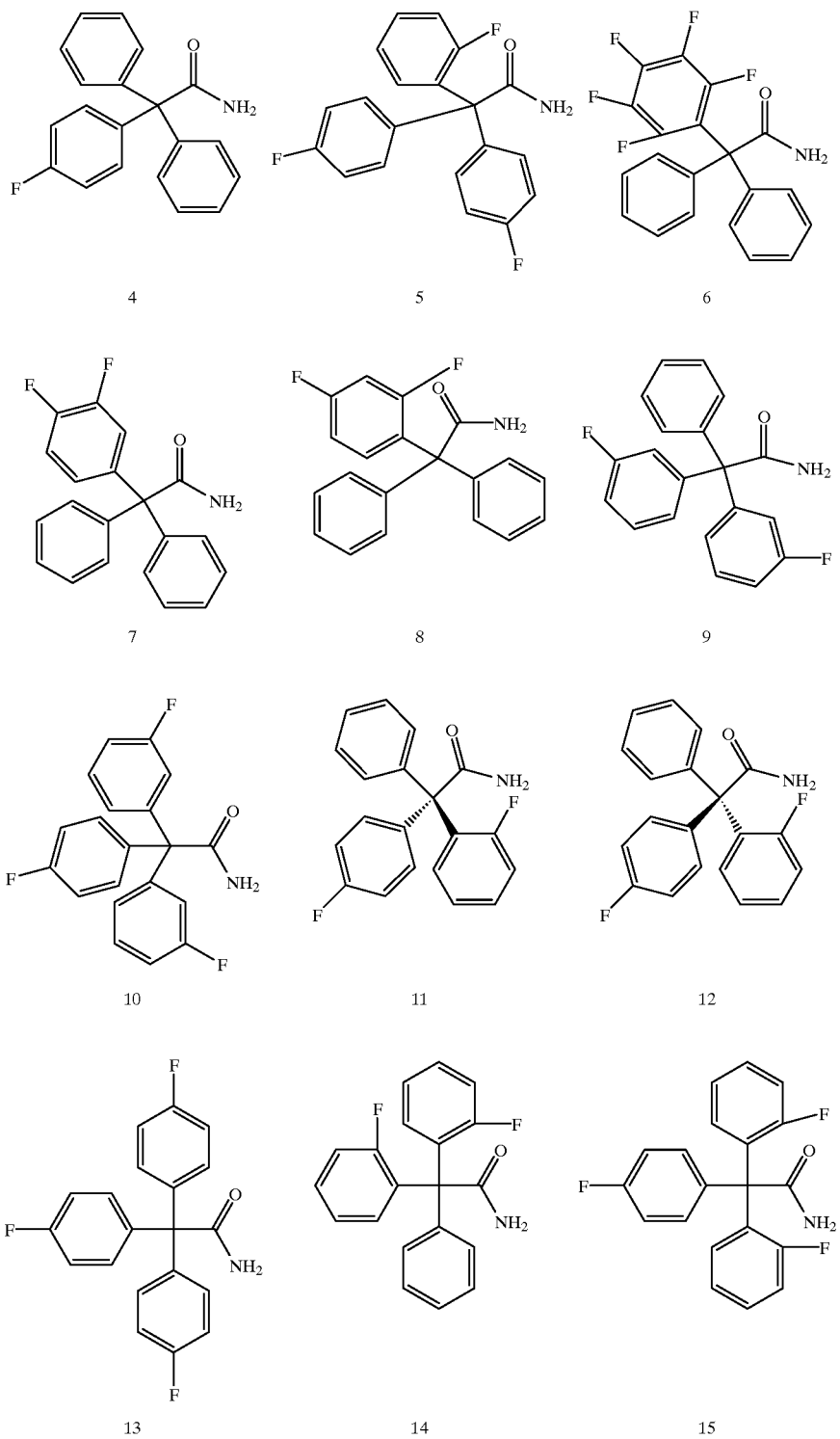

TABLE 1-continued

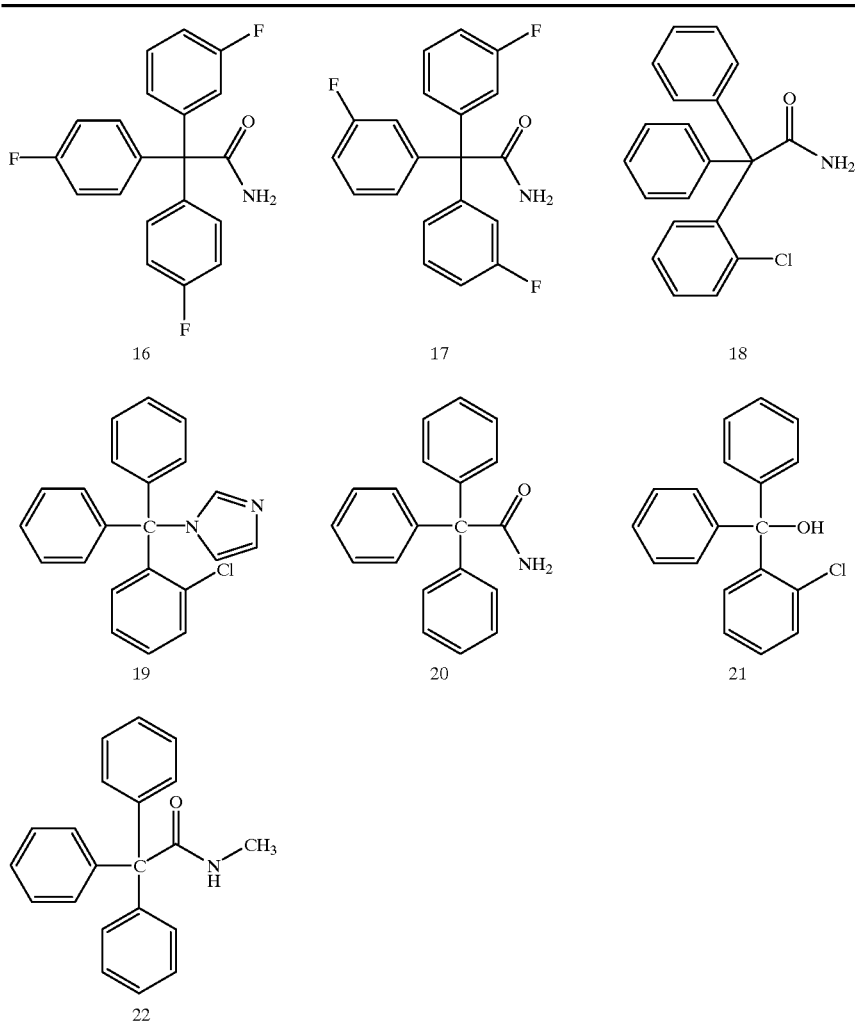

Compound Synthesis

The compounds of the invention can be prepared by techniques that are standard in the art of organic synthesis. Appropriate starting materials and reagent can be obtained commercially or they can be prepared by standard organic chemistry techniques. Preferred processes are illustrated by the specific examples. An exemplary synthetic route is provided in Scheme 1.

Scheme 1

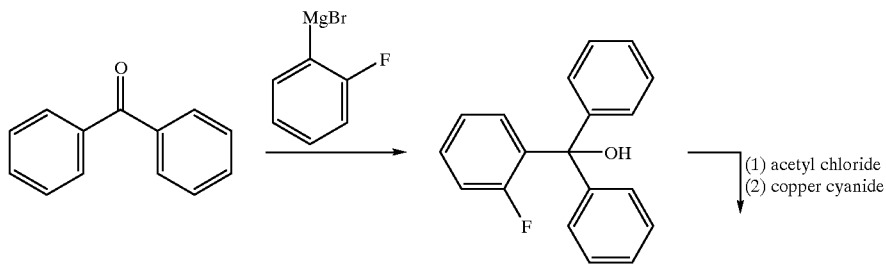

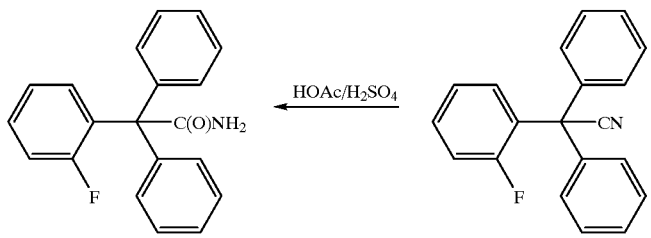

In Scheme 1, the synthesis of a fluorine-substituted triphenylacetamide proceeds from the corresponding fluorine-substituted triphenylmethanol that is prepared from a fluorine-substituted benzophenone and a reagent that adds a phenyl or fluorine-substituted phenyl moiety to the benzophenone ketone. The fluorine-substituted triphenylmethanol is subsequently converted to the corresponding fluorine-substituted triphenylacetonitrile by exposing the alcohol to acetyl chloride followed by copper cyanide. The acetamide can be formed by reacting the intermediate nitrile with a mixture of sulfuric and glacial acetic acids. Other synthetic routes leading to fluorine-substituted triphenylmethane species, particularly acetamides, are within the abilities of those skilled in the art.

Compound Stability

For compounds to act as pharmaceutically useful Gardos channel inhibitors, candidate compounds must demonstrate both acceptable bioavailability and stability in vivo. Compounds are judged to have a sufficient level of stability when at least 40% of an initial amount of the compound remains intact following a two hour incubation in a biological medium (e.g., microsome preparation). This level of stability is particularly important for treating a chronic syndrome such as sickle cell anemia. Subjects undergoing treatment for sickle cell anemia must be regularly dosed with the anti-sickling agent (e.g., the Gardos channel inhibitor) throughout the duration of their life. Among other concerns, such a lifelong dosage regimen presents a serious risk of variable patient compliance with the regimen. If the titer of the medication in the patient's system decreases as a result of poor compliance, this raises the risk of the occurrence of a sickle cell event and the concomitant pain and physical and physiological damage. Compounds having increased in vivo residence times and increased bioavailability allow for a simplified dosage regimen (i.e. fewer doses/day and/or less medication). Moreover, reducing the amount of compound administered carries with it the promise of reducing side effects resulting from the medication and/or its metabolites. Thus, it is highly desirable to provide Gardos channel inhibitors demonstrating good bioavailabilities and enhanced in vivo stabilities.

The stability of the compounds in various biological milieus can be assayed by methods known in the art. In one embodiment, the stability of the compounds is assayed in an in vitro preparation. In a preferred embodiment, the in vitro preparation is a liver microsome preparation. The results of such in vitro assays provide data relevant to the in vivo stability of the compounds of the invention. Other in vitro assays useful in assaying the stability of the compounds of the invention are known in the art.

In addition to in vitro methods, in vivo methods such as pharmacokinetic studies can be performed in a range of animal models. One or more compounds of the invention can be administered to an animal, preferably a rat, at different dosages and/or by different routes (e.g., i.v., i.p., p.o). Blood, urine and/or feces samples can be collected at serial time points and the samples assayed for the presence and/or concentration of the compound(s) of the invention and/or the metabolites of the compound(s).

Any appropriate quantity can be utilized to compare data from different compounds. Exemplary quantities include, half-life, bioavailability, amount of compound remaining intact after a predetermined time period and the like. In a preferred embodiment, the amount of compound remaining intact after a predetermined time period is utilized. As used herein, "intact" refers to compound that has not been metabolized or other wise degraded into a species different from the original compound.

In a preferred embodiment, the predetermined time period is from about two hours to about seventy-two hours, more preferably from about 4 hours to about twenty-four hours. In another preferred embodiment the amount of intact compound remaining after a predetermined time period of two hours is at least 40% of the initial sample, preferably at least 50% and more preferably at least 70%.

Any technique that allows the detection and, preferably, the quantitation of the compound(s) and/or metabolites is appropriate for use in assaying the compounds of the invention. These methods include, but are not limited to, spectrometric methods (e.g., NMR (e.g., $^{19}F$ NMR), MS, IR, UV/vis), chromatographic methods (e.g., LC, GC, HPLC) and hybrid methods utilizing both spectrometric and chromatographic methods (e.g., GC/MS, LC/MS, LC/MS/MS). Further, the methods can utilize detectable labels such as compounds of the invention that are labeled with radioisotopes (e.g., $^{3}H$, $^{15}N$, $^{14}C$) or fluorescent labels (e.g., fluorescein, rhodamine). Other methods for assaying the in vivo persistence of small organic molecules, particularly those applicable to bioactive molecules, will be apparent to those of skill in the art.

Compound Activity

To develop pharmaceutically useful Gardos channel inhibitors, candidate compounds must demonstrate acceptable activity towards the target channel. Compounds are judged to be sufficiently potent if they have an $IC_{50}$ towards the Gardos channel of no more than 30 nM.

As discussed above in the context of compound stability, this level of activity is particularly important for treating a chronic syndrome such as sickle cell anemia. The various concerns about patient compliance and side effects are well addressed by Gardos channel inhibitors having a potency towards the Gardos channel of 30 nM.

The activity of the compounds of the invention towards ion channels, such as the Gardos channel can be assayed utilizing methods known in the art. For example, see, Brugnara et al., *J. Biol. Chem.*, 268(12): 8760–8768 (1993). Utilizing the methods described in this reference, both the percent inhibition of the Gardos channel and the $IC_{50}$ of the compounds of the invention can be assayed.

In an exemplary assay, the inhibition by test compounds of an erythrocyte Gardos channel can be assayed using human red blood cells. The degree of inhibition can be measured using a detectable material such as $^{86}$Rb. In an exemplary assay, utilizing $^{86}$Rb, Gardos channel inhibition can be assayed by exposing red blood cells to $^{86}$Rb and a test compound and measuring the amount of $^{86}$Rb taken up by the cells. Numerous variations on this assay will be apparent to those of skill in the art.

The potency of the compounds of the invention can be assayed using erythrocytes by a method such as that disclosed by Brugnara et al., *J. Clin. Invest.*, 92: 520–526 (1993). Briefly, erythrocytes are exposed to a test compound and a $^{86}$Rb-containing medium. The initial rate of $^{86}$Rb transport can be calculated from a parameter such as the linear least square slope of $^{86}$Rb uptake by the cell(s). Inhibitory constants can be calculated by standard methods using computer-assisted nonlinear curve fitting.

Other methods for assaying the activity of ion channels and the activity of 30 agents that affect the ion channels are known in the art. The selection of an appropriate assay methods is well within the capabilities of those of skill in the art who. See, for example, Hille, B., IONIC CHANNELS OF EXCITEBLE MEMBRANES, Sinaner Associates, Inc. Sunderland, Mass. (1992).

The results of Gardos channel and erythrocyte inhibition assays utilizing compounds of the invention and other closely-related compounds are displayed in Table 2, below. The compound numbers in Table 2 are cross-referenced to the compound structures displayed in Table 1.

TABLE 2

| Cpd # | IC$_{50}$ Potency vs. Gardos (nM) | Est. IC$_{50}$ Potency vs. I$_{Ks}$ (nM) | % intact after 2 h | Selectivity (I$_{Ks}$ vs. Gardos) |
|---|---|---|---|---|
| 1 | 9 | 2000 | 64 | 220 |
| 2 | 15 | N.D | 80 | N.D |
| 3 | 12 | 1500 | 76 | 130 |
| 4 | 13 | N.D | 80 | N.D |
| 5 | 10 | 1400 | 71 | 140 |
| 6 | 37 | N.D | N.D | N.D |
| 7 | 14 | 1200 | 15 | 90 |
| 8 | 34 | 5700 | 39 | 170 |
| 9 | 30 | 3200 | 3 | 110 |
| 10 | 12 | 1300 | 59 | 110 |
| 11 | 5 | 1300 | 78 | 260 |
| 12 | 5 | 1800 | 44 | 360 |
| 13 | 14 | 1100 | 53 | 80 |
| 14 | 30 | N.D | 46 | N.D |
| 15 | 15 | N.D | 53 | N.D |
| 16 | 17 | 1900 | 57 | 110 |
| 17 | 13 | 4000 | 18 | 310 |
| 18 | 10 | 7300 | 6 | 730 |
| 19 (clotrimazole) | 100 | 820 | 4 | 8 |
| 20 | 50 | 1100 | 13 | 22 |
| 21 | 500 | 2600 | 35 | 5 |
| 22 | 100 | 2600 | 8 | 26 |

N.D. = Not Determined

Compound Selectivity

For compounds to act as pharmaceutically useful Gardos channel inhibitors, candidate compounds must demonstrate acceptable selectivity towards the target channel. Compounds having a selectivity towards the Gardos channel, as measured by the ratio of a compound IC$_{50}$ towards I$_{Ks}$ vs. its IC$_{50}$ towards the Gardos channel of at least 80 are judged to be sufficiently selective. Recordings of I$_{Ks}$ current were made using the whole cell patch clamp methodology on guinea pig myocytes as described in Turgeon et al., *Circulation Research* 75: 879–86 (1994).

The selectivity of a particular compound for the Gardos channel relative to another potassium ion channel is conveniently determined as a ratio of two compound binding-related quantities (e.g., IC$_{50}$). In a preferred embodiment, the selectivity is determined using the activities determined as discussed above, however, other methods for assaying the activity of ion channels and the activity of agents that affect the ion channels are known in the art. The selection of appropriate assay methods is well within the capabilities of those of skill in the art. See, for example, Hille, B., IONIC CHANNELS OF EXCITABLE MEMBRANES, Sinaner Associates, Inc. Sunderland, Mass. (1992).

The results of selectivity determinations for the compounds of the invention and other closely-related compounds are displayed in Table 2. The selectivity of the compounds for the Gardos channel was determined relative to I$_{Ks}$, an exemplary potassium ion channel. The compound numbers in Table 2 are cross-referenced to the compound structures displayed in Table 1.

As can be seen from the results displayed above, the compounds of the invention demonstrate marked selectivity for the Gardos channel versus other potassium ion channels (e.g., I$_{Ks}$) Moreover, the compounds of the invention are potent inhibitors of the Gardos channel. Additionally, the in vivo half-lives of these compounds are demonstrably enhanced relative to non-fluorinated compounds such as clotrimazole.

In one embodiment, the compounds of the invention are potent, selective and stable inhibitors of potassium flux, such as that mediated by the Gardos channel.

The compounds of the invention are preferably stable in a biological medium, such as an in vitro microsomal enzyme preparation with at least 40% of the intact compound remaining after a two hour incubation in the biological milieu, preferably greater than 50% and more preferably greater than 70%.

While not wishing to be bound by any particular theory of operation, it is presently believed that certain structural features of the compounds of the invention (i.e. replacement of hydrogen with fluorine) are presently implicated in the stability, selectivity and potency of these compounds. Thus, in a preferred embodiment, the inhibitors of the invention comprise an aryl moiety, wherein at least one hydrogen atom of the aryl moiety is replaced by a radical comprising a fluorine atom. In this embodiment, the invention encompasses fluorinated derivatives of compounds that inhibit potassium ion flux, particularly those having Gardos channel inhibitory activity (e.g., antimycotic agents, e.g., miconazole, econazole, butoconazole, oxiconazole and sulconazole). Other agents that have potassium ion channel inhibitory activity, and particularly Gardos channel inhibitory activity and at least one aryl moiety bearing at least one fluorine atom are within the scope of the present invention.

In a preferred embodiment, the aryl moiety is a phenyl group. In another preferred embodiment, the aryl moiety is a constituent of a triphenylmethyl group.

The compound(s) of the invention can be administered per se or in the form of a pharmaceutical composition wherein the active compound(s) is in admixture with one or more pharmaceutically acceptable carriers, excipients or diluents. Thus, in addition to compounds that affect cellular ion fluxes (e.g., Gardos channel inhibiting activity), the present invention also provides pharmaceutical formulations that contain the compounds of the invention.

Pharmaceutical Formulations

In a second aspect, the invention provides a pharmaceutical formulation comprising a compound of the invention according to Formula (I) admixed with a pharmaceutically acceptable excipient. In a preferred embodiment, the compounds are those according to Formula (II) and more preferably according to Formula (III).

The compounds described herein, or pharmaceutically acceptable addition salts or hydrates thereof, can be formulated so as to be delivered to a patient using a wide variety of routes or modes of administration. Suitable routes of administration include, but are not limited to, inhalation, transdermal, oral, ocular, rectal, transmucosal, intestinal and parenteral administration, including intramuscular, subcutaneous and intravenous injections.

The compounds described herein, or pharmaceutically acceptable salts and/or hydrates thereof, may be administered singly, in combination with other compounds of the invention, and/or in cocktails combined with other therapeutic agents. The choice of therapeutic agents that can be co-administered with the compounds of the invention will depend, in part, on the condition being treated.

For example, when administered to patients suffering from sickle cell disease, the compounds of the invention can be administered in cocktails containing agents used to treat the pain, infection and other symptoms and side effects commonly associated with sickle cell disease. Such agents include, e.g. analgesics, antibiotics, etc. The compounds can also be administered in cocktails containing other agents that are commonly used to treat sickle cell disease, including butyrate and butyrate derivatives (Perrine et al., *N. Engl. J. Med.* 328(2): 81–86 (1993)); hydroxyurea (Charache et al., *N. Engl. J. Med.* 323(20): 1317–1322 (1995)); erythropoietin (Goldberg et al, *N. Engl. J. Med.* 323(6): 366–372 (1990)); and dietary salts such as magnesium (De Franceschi et al., *Blood* 88(648a): 2580(1996)).

Pharmaceutical compositions for use in accordance with the present invention can be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention can be formulated in aqueous solutions, preferably in physiologically compatible buffers such as Hanks's solution, Ringer's solution, or physiological saline buffer. In a presently preferred embodiment, the formulation comprises water and an alcohol and/or glycol. Other useful components of this formulation include, for example, surfactant, emulsifiers and materials such as ethoxylated oils. An exemplary formulation comprises a compound of the invention, poly (ethyleneglycol) 400, ethanol and water in a 1:1:1 ratio. Another exemplary formulation comprises a compound of the invention, water, poly(ethyleneglycol) 400 and Cremophor-EL.

For transmucosal administration (e.g., buccal, rectal, nasal, ocular, etc.), penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be combined with a solid excipient, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents may be added, such as the cross-linked polyvinyl pyrrolidone, agar, or alginic acid or a salt thereof such as sodium alginate.

Pharmaceutical formulations for parenteral administration include aqueous solutions of the active compounds in water-soluble form, such as those described above for intravenous administration. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Effective Dosages

Pharmaceutical compositions suitable for use with the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to reduce sickle cell dehydration and/or delay the occurrence of erythrocyte sickling or distortion in situ, such compositions will contain an amount of active ingredient effective to achieve this result. Determination of an effective amount is well within the capabilities of those skilled in the art, especially in light of the detailed disclosure herein.

For any compound described herein, the therapeutically effective amount can be initially determined from cell culture assays. Target plasma concentrations will be those concentrations of active compound(s) that are capable of inducing inhibition of the Gardos channel. In preferred embodiments, the Gardos channel activity is at least 25% inhibited. Target plasma concentrations of active compound (s) that are capable of inducing at least about 50%, 75%, or even 90% or higher inhibition of the Gardos channel potassium flux are presently preferred. The percentage of inhibition of the Gardos channel in the patient can be monitored to assess the appropriateness of the plasma drug concentration achieved, and the dosage can be adjusted upwards or downwards to achieve the desired percentage of inhibition.

As is well known in the art, therapeutically effective amounts for use in humans can also be determined from animal models. For example, a dose for humans can be formulated to achieve a circulating concentration that has been found to be effective in animals. A particularly useful animal model for sickle cell disease is the SAD-1 mouse model (Trudel et al., $EMBO$ $J$. 11: 31573165 (1991)). The dosage in humans can be adjusted by monitoring Gardos channel inhibition and adjusting the dosage upwards or downwards, as described above.

A therapeutically effective dose can also be determined from human data for compounds which are known to exhibit similar pharmacological activities, such as clotrimazole and other antimycotic agents (see, e.g., Brugnara et al., $JPET$ 273:266272 (1995)); Benzaquen et al., $Nature$ $Medicine$ 1: 534–540 (1995); Brugnara et al., $J.$ $Clin.$ $Invest.$ 97(5): 1227–1234 (1996)). The applied dose can be adjusted based on the relative bioavailability and potency of the administered compound as compared with clotrimazole.

Adjusting the dose to achieve maximal efficacy in humans based on the methods described above and other methods as are well-known in the art is well within the capabilities of the ordinarily skilled artisan.

In the case of local administration, the systemic circulating concentration of administered compound will not be of particular importance. In such instances, the compound is administered so as to achieve a concentration at the local area effective to achieve the intended result.

For use in the prophylaxis and/or treatment of sickle cell disease, including both chronic sickle cell episodes and acute sickle cell crisis, a circulating concentration of administered compound of about 0.001 ΓM to 20 ΓM is considered to be effective, with about 0.01 ΓM to 5 ΓM being preferred.

Patient doses for oral administration of the compounds described herein, which is the preferred mode of administration for prophylaxis and for treatment of chronic sickle cell episodes, typically range from about 1 mg/day to about 10,000 mg/day, more typically from about 10 mg/day to about 1,000 mg/day, and most typically from about 50 mg/day to about 500 mg/day. Stated in terms of patient body weight, typical dosages range from about 0.01 to about 150 mg/kg/day, more typically from about 0.1 to about 15 mg/kg/day, and most typically from about 1 to about 10 mg/kg/day.

For other modes of administration, dosage amount and interval can be adjusted individually to provide plasma levels of the administered compound effective for the particular clinical indication being treated. For example, if acute sickle crises are the most dominant clinical manifestation, in one embodiment, a compound according to the invention can be administered in relatively high concentrations multiple times per day. Alternatively, if the patient exhibits only periodic sickle cell crises on an infrequent, periodic or irregular basis, in one embodiment, it may be more desirable to administer a compound of the invention at minimal effective concentrations and to use a less frequent administration regimen. This will provide a therapeutic regimen that is commensurate with the severity of the individual's sickle cell disease.

Utilizing the teachings provided herein, an effective prophylactic or therapeutic treatment regimen can be planned which does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

Compound Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl el al., In.

The Pharmacological Basis of Therapeutics, Ch.1, p.1, 1975. The exact formulation, route of administration and dosage can be chosen by the individual physician in view of the patient's condition and the particular method in which the compound is used.

Methods

In addition to the compounds and pharmaceutical formulations discussed in detail above, the present invention provides a number of methods in which the compounds of the invention find use. The methods range from those that might be used in a laboratory setting to probe the basic mechanisms of, for example, pharmacokinetics, drug activity, disease origin and progression and the like.

Thus, in a third aspect, the invention provides a method of inhibiting potassium flux of a cell. The method comprises, contacting a cell with an effective amount of a compound having a structure according to Formula I. In a preferred embodiment, the compounds have a structure according to Formula II and more preferably according to Formula III.

This aspect of the invention has a wide range of uses, but it is preferred as a modality for the study of the basic mechanisms underlying potassium flux and the mechanism of activity of agents that modulate this flux. Further, the compounds of the invention can be utilized as tools in the discovery of new agents that modulate potassium flux. For example, the compounds of the invention can be utilized in assays, such as competitive assays, to test the efficacy of putative inhibitors of potassium flux. These methods of the invention can be performed both in vitro and in vivo. Assays according to the present invention can be carried out by, for example, modifying art-recognized methods to allow the incorporation of the compounds of the invention into them. Such modification is well within the skill of those of skill in the art.

In another preferred embodiment, this method is used therapeutically to treat or prevent a condition that can be positively affected by modulating potassium flux. In a presently preferred embodiment, the condition is sickle cell disease.

In a fourth aspect, the invention provides a method for reducing erythrocyte dehydration. This method comprises, contacting an erythrocyte with an effective amount of a compound having a structure according to Formula I. In a preferred embodiment, the compounds have a structure according to Formula II and more preferably according to Formula III.

This aspect of the invention can be used for a range of purposes including, for example, study of the mechanism of erythrocyte dehydration, investigation of compounds that inhibit or reverse erythrocyte dehydration and the treatment or prevention of conditions associated with erythrocyte dehydration.

In a fifth aspect, the invention provides a method of treating or preventing sickle cell disease. The method comprises administering to a subject suffering sickle cell disease a therapeutically effective amount of a compound having a structure according to Formula I. In a preferred embodiment, the compounds have a structure according to Formula II and more preferably according to Formula III.

This aspect of the invention can be utilized to prevent the onset of acute sickle cell events or to ameliorate the effects of these events. Further, the method can be used to treat and/or prevent chronic sickle cell disease. The method can make use of the compounds of the invention per se or, preferably, the pharmaceutical formulations of the invention. The relevant modes of administration, choice of dosage levels and frequency of dosing are discussed above.

In a sixth aspect, the present invention provides a method for enhancing the resistance to degradation in a biological medium of a potassium channel inhibitor, comprising a phenyl moiety. The method comprises substituting a radical comprising a phenyl atom for a hydrogen atom on the phenyl radical of the inhibitor.

The method can be practiced using potassium channel inhibitors having a range of structures. The only limitation on the structure of the inhibitor is that a phenyl ring must be present as a component of the inhibitor's structure. In a preferred embodiment, the phenyl ring is a component of a triphenylmethyl radical. In a further preferred embodiment, the degradation is reduced to less than 60% of the compound being degraded after being in contact with a biological medium for two hours.

The substitution of the fluorine radical for a hydrogen can be accomplished by the methods disclosed herein or by other methods standard in organic chemistry. A wide range of compounds having the required substitution can be assembled from fluoro-aryl compounds that are readily available from commercial suppliers such as Aldrich Chemical Co.(Milwaukee, Wis.). Additionally, numerous standard synthetic routes exist for the facile assembly of compound appropriate starting materials for compounds assembled in accordance with the method of the invention.

In choosing targets to convert to fluoro-derivatives, one of skill will understand that it is desirable to begin with aryl-containing compounds having known activity towards the Gardos channel. Many art-recognized agents having antimycotic properties have demonstrable Gardos channel activity. Thus, one of skill would choose agents having the antimycotic activity, or analogues of these compounds, to prepare fluorinated analogues of. Assaying the new agents for potency and resistance to biological degradation can be accomplished routinely by one of skill in the art utilizing the methods provided herein in addition to those known in the art. Additionally, through routine experimentation utilizing these methods, one of skill can quickly assay one or more aryl-containing molecules for activity towards the Gardos channel. Fluoro-derivatives of promising targets can then be prepared and assayed, as discussed above.

Optimized Pharmaceutical Properties a. Metabolic resistance

The present triphenylacetamide-based inhibitors of the Gardos channel, in which one or more of the phenyl groups is substituted with one or more fluorine atoms or fluorine-containing moieties, have surprisingly high metabolic stabilities relative to known inhibitors such as clotrimazole. For example, clotrimazole 19 is 94.2% degraded after incubating two hours in a liver microsome preparation. In contrast, representative fluorinated compounds of the invention, such as 3 and 5 are only 24% and 29% degraded after a similar incubation. These fluorinated triphenylactamides are also notably more stable than their non-fluorinated analogues. For example, compound 20 is 87% degraded after a similar incubation.

Although a general trend towards enhanced stability is observed upon fluoro substitution, this does not hold true for all fluorinated derivatives. For example, a triphenylacetamide substituted on two of the phenyl rings in the 3- and 3'-positions 9 was 97% degraded after two hours in a microsomal preparation. Thus, in this instance, fluoro substitution apparently increased the amount of degradation relative to both clotrimazole and a non-fluorinated triphenylacetamide.

Similarly, analogous compounds bearing two fluoro substituents on one ring were also rapidly degraded. For example, after two hours in a microsome preparation, derivatives substituted at the 2-, 4- (8) and 3-, 4-positions (7) were 61% and 85% degraded, respectively. Furthermore, certain compounds which were monosubstituted at each of the three phenyl rings were also rapidly degraded. For example, a derivative substituted at the 3-, 3'- and 3"-positions (17) was 82% degraded after two hours in a microsome preparation.

In view of the above, it has been discovered that only selected substitution patterns impart the necessary level of stability to fluorinated triphenylacetamides. A similar variation in compound potency and selectivity with substitution pattern is also observed.

b. Potency

An unexpected result of substituting fluorine for hydrogen on the phenyl rings is a notably enhanced potency of the compounds of the invention for the Gardos channel relative to clotrimazole and non-fluorinated triphenylacetamides. For example, a non-fluorinated triphenylacetamide 20 has an $IC_{50}$ of 50 nM towards the Gardos channel. In contrast, an analogous monofluorinated triphenylacetamide 2 has an $IC_{50}$ of 15 nM, reflecting a 330% improvement in potency.

Although a general trend towards improved potency is observed for the fluorinated triphenylacetamide derivatives, certain substitution patterns appear to more profoundly improve the potency relative to the unsubstituted parent compound. A particular aspect of this general trend is that derivatives in which more than one ring is substituted are generally more potent than those in which only one ring is substituted. For example, compound 8, has two fluoro substituents on a single ring at a 2- and the 4-positions and an $IC_{50}$ of 34 nM. In contrast, compound 12, has one fluoro substituent on one ring at a 2-position, a fluoro substituent on another ring at the 4'-position, and an $IC_{50}$ of 5 nM. This reflects an improvement in potency of 12 over 8 of almost 700%. Moreover, compound 12 has a potency 1000% greater than that of the non-fluorinated parent compound 20. This reflects an increase in potency over clotrimazole of 2000%!

In spite of the trend towards increasing potency, the degree of improvement in compound potency is not predictable, a priori, from the number of substituents per ring. For example, compound 9 has a fluoro substituent on one ring at a 3-position, a fluoro substituent on another ring at a 3'-position and an $IC_{50}$ of 30 nM. A similar compound 11, having a fluoro substituent on one ring at a 2-position, a fluoro substituent on another ring at the 4'-position and an $IC_{50}$ of 5 nM, an increase in potency of 11 over 9 of 600%.

As discussed above, it has been discovered that the potency of fluorinated triphenylacetamides towards the Gardos channel can be manipulated by judicious choice of both the number of fluoro substituents and their placement on the phenyl rings of these compounds. Surprisingly, similar effects are observed for the selectivity towards the Gardos channel of these compounds c. Selectivity In addition to potency and bioavailability, a pharmaceutical agent for treating sickle cell anemia by inhibiting ion flux must be selective for the ion channel that is its target. Interaction of the agent with channels other than the target will likely cause unwanted and potentially dangerous side-effects. For example, clotrimazole and some of its analogs are known to interact with the slow component of the delayed rectifier potassium current in myocytes, $I_{Ks}$. Blockade of this current is linked to sudden death due to ventricular fibrillation (Turgeon et al., *Circulation Research* 75: 879–86 (1994)). Therefore, compounds exhibiting selectivity for the Gardos channel over $I_{Ks}$ will likely prove to be safer and more efficacious pharmaceutical agents.

Yet another unexpected result of fluorinating one or more of the rings of Gardos channel inhibitors is an increased selectivity of these compounds for the Gardos channel relative to other potassium channels. Several of the fluoro substituted triphenylacetamides of the invention demonstrate a dramatically improved selectivity towards the Gardos channel versus $I_{Ks}$, relative to both clotrimazole and the non-fluorinated parent triphenylacetamide. For example, compounds 3 and 5 are approximately 16-fold and 18-fold more selective for the Gardos channel versus $I_{Ks}$ than clotrimazole. Moreover, these compounds are both approximately 6-fold more selective for the Gardos channel than the unsubstituted triphenylacetamide parent 20.

It has now been discovered that fluorine-substituted triphenylmethane derivatives, particularly fluorine-substituted nitrogenous compounds such as triphenylacetamides effectively inhibit the Gardos channel of erythrocytes. Moreover, the fluorine-substituted compounds display a resistance to degradation in a biological medium that is enhanced to a surprising degree relative to the corresponding compounds that are not substituted with fluorine.

The compounds, compositions and methods of the present invention are further illustrated by the examples that follow. These examples are offered to illustrate, but not to limit the claimed invention.

EXAMPLES

Example 1 illustrates methods for the synthesis and characterization of compounds of the invention. The compounds of the invention were isolated in substantially pure form and in good yields utilizing the methods detailed in this Example.

Example 2 illustrates the assay of the compounds of the invention for their resistance to degradation in a biological medium. In this Example, human liver microsomes form the biological medium. The compounds of the invention were found to display a remarkable resistance to degradation by the microsome preparation, relative to non-fluorinated triphenylmethyl compounds.

Example 3 sets forth a pharmacokinetic study of the compounds of the invention in the rat. The fluorinated compounds of the invention were found to exhibit an in vivo half-life that was enhanced relative to non-fluorinated derivatives.

Example 4 describes a bioassay for measuring the inhibition of potassium channel (Gardos channel) by the compounds of the invention.

Example 1

This Example illustrates methods for the synthesis and characterization of compounds of the invention. The compounds of the invention were isolated in substantially pure form and in good yields utilizing the methods detailed below. The example provides methods of general scope that can be used to synthesize compounds of the invention other than those specifically exemplified.

1.1 Materials and Methods

Reagents were used as received unless otherwise stated. The method of Franco et al., *J. Chem. Soc. Perkins Trans. II*, 443 (1988), was used to prepare non-commercial fluorophenyllithium reagents and fluorobenzophenones. All moisture-sensitive reactions were performed under a nitrogen atmosphere using oven dried glassware. Reactions were monitored by TLC on silica gel 60 $F_{254}$ with detection by charring with Hanessian's stain (Khadem et al., *Anal. Chem.*, 1958, 30, (1965)). Column chromatography was carried out using Selecto silica gel (32–63 ΓM). Melting points were determined on an Electrothermal IA9000 unit and are uncorrected. $^1H$ (300 MHz) and $^{19}F$ (282 MHz) spectra were recorded on a Varian (Gemini 2000) NMR machine at room temperature in $CDCl_3$. Tetramethylsilane was used as the internal reference. Chiral separation of compound 1 was performed by Chiral Technologies using a CHLIRACEL$^\leq$ OD-R column and acetonitrile/water as the eluant.

1.2 Preparation of Compound 1

Compound 1 was prepared in 28% yield in four steps from commercially vailable precursors.

1.2a Synthesis of (2-fluorophenyl)-(4-fluorophenyl) phenylmethanol

Phenylmagnesium bromide (1.83 mL, 5.5 mmol) was added dropwise to a tirring solution of 2,4'-difluorobenzophenone (1.09 g, 5.0 mmol) in t-butylmethyl ether (12 mL) at room temperature ("rt,"~25° C.). After the addition was complete the reaction was heated at reflux for 3 h. The solution was cooled to rt and was poured in to ice cold 1.0 M HCl (aq) (20 mL). The organics were extracted with EtOAc (3×10 mL) and dried ($Na_2SO_4$). Concentration under reduced pressure gave the desired product (2-fluorophenyl)-(4-fluorophenyl)phenylmethanol as a pale brown oil which was used in the next reaction without any further purification.

1.2b Synthesis of (2-fluorophenyl)-(4-fluorophenyl) phenylacetonitrile (2-Fluorophenyl)-(4-fluorophenyl)phenylmethanol (1.47 g, 5.0 mmol) was added to a 20% solution of acetyl chloride in dichloromethane (10 mL) at rt. The resulting solution was stirred for 12 h after which the solvent was removed by evaporation. Toluene (2×20 mL) was added to the residue and evaporated to afford crude 2-fluorophenyl-(4-fluorophenyl)phenylchloromethane which was used without purification in the next step.

Copper cyanide (0.50 g, 5.5 mmol) was added to the residue and the resultant mixture was heated at 130° C. for 2.5 h. Once the reaction had cooled to approximately 110° C. toluene (30 mL) was added and the mixture was stirred vigorously for 10 min. The mixture was filtered and the solvent was removed under reduced pressure. Hot hexane (30 mL) was added to the crude material and the mixture was stirred vigorously for 30 min. Filtration and washing with more hexane gave the desired cyano product as a white solid, which was used without further purification.

1.2c Synthesis of (2-fluorophenyl)-(4-fluorophenyl) phenylacetamide (1)

A solution of concentrated sulfuric acid (10 mL) and glacial acetic acid (10 mL) was added to crude (2-fluorophenyl)-(4-fluorophenyl)phenylacetonitrile (1.48 g, 5.0 mmol) at rt. The resulting orange solution was stirred and heated at 130° C. for 3 h. The reaction was cooled to 0° C. and was neutralized by the dropwise addition of ammonium hydroxide. Water was added (30 mL) and the organics were extracted with chloroform (3×30 mL). The organic fractions were combined and washed sequentially with water (2×10 mL) and brine (20 mL). The organic phase was dried ($Na_2SO_4$) and concentrated under reduced pressure. Hexane (30 mL) was added to the resulting light brown oil to initiate precipitation. The precipitate was ground up and washed sequentially with hot hexane (30 mL). Crystallization from hexane/dichloromethane gave the desired product (2-fluorophenyl)-(4-fluorophenyl)phenylacetamide as a white crystalline solid (0.45 g, 1.4 mmol, 28%, 4 steps).

1.3 Preparation of Compound 3

Compound 3 was prepared in three steps from commercially available precursors in 58% yield.

1.3a Synthesis of bis(4-fluorophenyl)phenylmethanol

Phenylmagnesium bromide (100 mL, 0.1 mol) was added dropwise to a stirring solution of 4,4'-difluorobenzophenone (20 g, 0.092 mol) in t-butylmethyl ether (150 mL) at rt. After the addition was complete the reaction was heated at reflux for 3 h. The solution was cooled to rt and was poured in to ice cold aqueous 1.0 M HCl (100 mL). The organics were extracted with EtOAc (2×50 mL) and dried ($Na_2SO_4$). Concentration under reduced pressure gave bis(4-fluorophenyl)phenylmethanol as a pale brown oil. After drying in vacuo for 2 h the crude material was used in the next reaction without any further purification.

1.3b Synthesis of bis(4-fluorophenyl)phenylacetonitrile

Bis(4-fluorophenyl)phenylmethanol (0.092 mol) was added to a 20% solution of acetyl chloride in dichloromethane (50 mL) at rt. The resulting purple solution was stirred for 12 h after which the solvent was removed by evaporation. Toluene (100 mL) was added to the residue and then evaporated, affording crude bis(4-fluorophenyl)phenylchloromethane which was used without purification in the following step.

Copper cyanide (8.24 g, 0.11 mol) was added to the crude residue and the mixture was heated at 140° C. for 3 h. The reaction was cooled to 100° C. and toluene (100 mL) was added. The resulting mixture was stirred vigorously for 10 min, cooled to rt, filtered through a short pad of silica and the solvent was removed under reduced pressure to afford a brown solid. Hot hexane (100 mL) was added to the powdered crude material and the mixture was stirred vigorously for 4 h. Filtration and washing with additional hexane gave the desired bis(4-fluorophenyl)phenylacetonitrile as a white solid (18.9 g, 67%).

1.3c Synthesis of bis(4-fluorophenyl)phenylacetamide (3)

A solution of concentrated sulfuric acid (50 mL) and glacial acetic acid (50 mL) was added to bis(4-fluorophenyl) phenylacetonitrile (18.9 g, 0.06 mol) at rt. The resulting orange solution was stirred and heated at 130° C. for 3 h. The reaction was cooled to 0° C., poured into ice water (150 mL) and neutralized with ammonium hydroxide. The organics were extracted with chloroform (3×100 mL), combined and washed with brine (2×50 mL). The organics were dried ($Na_2SO_4$) and concentrated under reduced pressure to afford a yellow-orange solid. The solid was stirred with hot hexane (100 ml) for 30 min and filtered. Crystallization from dichloromethane/hexane gave bis(4-fluorophenyl) phenylacetamide (3) as a white crystalline solid (16.9 g, 0.052 mol, 87%).

1.4 Preparation of Compound 5

Compound 5 was prepared in 66% yield in four steps from commercially available precursors.

1.4a Synthesis of bis(4-fluorophenyl)-2-fluorophenylmethanol p-Fluorophenylmagnesium bromide (124 mL, 0.12 mol) was added dropwise to a stirring solution of 2,4'-difluorobenzophenone (24.5 g, 0.11 mol) in t-butylmethyl ether (100 mL) at rt. After the addition was complete the reaction was heated at reflux for 3 h. The solution was then cooled to rt and was poured in to ice cold 1.0 M HCl (aq)

(100 mL). The organics were extracted with EtOAc (3×70 mL) and dried (Na$_2$SO$_4$). Concentration under reduced pressure gave the desired product bis(4-fluorophenyl)-2-fluorophenylmethanol as a pale yellow oil which was used in the next reaction without any further purification.

1.4b Synthesis of bis(4-fluorophenyl)-2-fluorophenylacetonitrile

A 20% solution of acetyl chloride in dichloromethane (60 mL) was added to the crude bis(4-fluorophenyl)-2-fluorophenylmethanol at rt. The resulting solution was stirred for 12 h after which the solvent was removed by evaporation. Toluene (100 mL) was added to the residue and was then evaporated to afford crude bis(4-fluorophenyl)-2-fluorophenylchloromethane which was used without purification in the next step.

Copper cyanide (12 g, 0.13 mol) was added to the crude material and the resulting mixture was heated at 160° C. for 3 h. The reaction was cooled to approximately 110° C., toluene (100 mL) was added and the mixture was stirred vigorously for 10 min. The mixture was cooled, filtered through a short silica plug and concentrated under reduced pressure. Hot hexane (100 mL) was added to the crude material and the mixture was stirred vigorously for 30 min. Filtration and washing with more hexane gave the desired bis(4-fluorophenyl)-2-fluorophenylacetonitrile as a white solid (25.3 g, 70%).

1.4c Synthesis of bis(4-fluorophenyl)-2-fluorophenylacetamide (5)

A solution of concentrated sulfuric acid (10 mL) and glacial acetic acid (10 mL) was added to bis(4-fluorophenyl)-2-fluorophenylacetonitrile (5.0 g, 0.015 mol) at rt. The resulting orange solution was stirred and heated at 130° C. for 2 h. The reaction was cooled to 0° C. and was poured onto ice (50 g). The resulting mixture was neutralized by the dropwise addition of ammonium hydroxide. CH$_2$Cl$_2$ (100 mL) was added and the organics were extracted with additional CH$_2$Cl$_2$ (3×30 mL). The combined organic fractions were washed sequentially with water (2×10 mL) and brine (20 mL). The organic phase was dried (Na$_2$SO$_4$) and concentrated under reduced pressure to afford a yellow/orange solid. The solid was powdered and washed repeatedly with hot hexane (50 ml) until no coloration was evident in the filtrate. Crystallization from hexane/dichloromethane gave the desired product bis(4-fluorophenyl)-2-fluorophenylacetamide 5 as a white crystalline solid (4.98 g, 0.0145 mol, 94%).

1.5 Preparation of Compound 16

Compound 16 was prepared in 11% yield in four steps from commercially available precursors.

1.5a Synthesis of bis(4-fluorophenyl)-3-fluorophenylmethanol n-Butyllithium (4 mL, 10 mmol) was added dropwise to a stirring solution of bromo-3-fluorobenzene (1.75 g, 10 mmol) in THF (25 mL) at −78° C. After 20 mins 4,4'-benzophenone (1.96 g, 9 mmol) was added. The reaction was allowed to warm to 0° C. over a 30 min period. Saturated NH$_4$Cl (aq) (30 mL) was added and stirring was continued for 30 min. EtOAc (20 mL) was added, the organics were separated, washed with brine (20 mL), dried (Na$_2$SO$_4$) and concentrated under reduced pressure. The residue was purified by column chromatography (100% hexane to 100% CH$_2$Cl$_2$) to afford bis(4-fluorophenyl)-3-fluorophenylmethanol (2.81 g, 92%).

1.5b Synthesis of bis(4-fluorophenyl)-3-fluorophenylacetonitrile

Bis(4-fluorophenyl)-3-fluorophenylmethanol (999 mg, 3.18 mmol) was added to a 20% solution of acetyl chloride in dichloromethane (10 mL) at rt. The resulting purple solution was stirred for 12 h after which the solvent was removed by evaporation. Toluene (20 mL) was added to the residue and then evaporated affording crude bis(4-fluorophenyl)-3-fluorophenylchloromethane which was used in the next step without purification.

Copper cyanide (344 mg, 3.82 mmol) was added to the crude material and the resulting mixture was heated at 140° C. for 3 h. The reaction was cooled to approximately 110° C., toluene (50 mL) was added and the mixture was stirred vigorously for 10 min. The mixture was cooled to rt, filtered through a short pad of silica and the solvent was removed under reduced pressure to afford a beige solid. Hot hexane (100 mL) was added to the powdered crude material and the mixture was stirred vigorously for 1 h. Filtration and washing with additional hexane gave bis(4-fluorophenyl)-3-fluorophenylacetonitrile as a white solid which was used without further purification.

1.5c Synthesis of bis(4-fluorophenyl)-3-fluorophenylacetamide (16)

A solution of concentrated sulfuric acid (10 mL) and glacial acetic acid (10 mL) was added to bis(4-fluorophenyl)-3-fluorophenylacetonitrile (3.18 mmol) at rt. The resulting orange solution was stirred and heated at 130° C. for 3 h. The reaction was cooled to 0° C., poured into ice water (50 mL) and neutralized with ammonium hydroxide. The organics were extracted with chloroform (3×50 mL). The organics fractions were combined washed with brine (2×20 mL), dried (Na$_2$SO$_4$) and concentrated under reduced pressure to afford a yellow-orange solid. The solid was stirred with hot hexane (50 ml) for 30 mins and filtered. Crystallization from dichloromethane/hexane gave the desired product bis(4-fluorophenyl)-3-fluorophenylacetamide 16 as a white crystalline solid (147 mg, 0.43 mmol, 11%, 4 steps).

1.6 Compound Characterization by $^1$H and $^{19}$F NMR Spectroscopy and Melting Point The compounds of the invention were characterized by a combination of $^1$H and $^{19}$F NMR spectroscopy and the compound melting points were determined.

1: $^1$NMR Γ(CHCl$_3$): 7.39–7.26 (8H, m), 7.15–6.90 (5H, m), 5.83 (1H, brs), 5.72 (1H, brs); $^{19}$F NMR Γ(CHCl$_3$): −103.4 (1F, s), −115.8 (1F, s); m.p 180–181° C.

2: $^1$H NMR Γ(CHCl$_3$): 7.37–7.28 (6H, m), 7.15–7.05 (2H, m), 6.93 (1H, dt, J=8 and 2 Hz), 5.90 (1H, brs), 5.68 (1H, brs); $^{19}$F NMR Γ(CHCl$_3$): −103.4 (1F, m); m.p 210° C.

3: $^1$H NMR Γ(CHCl$_3$): 7.37–7.20 (9H, m), 7.04–6.91 (4H, m), 5.81 (1H, brs), 5.71 (1H, brs); $^{19}$F NMR Γ(CHCl$_3$): −115.7 (2F, s); m.p 180–181° C.

4: $^1$H NMR Γ(CHCl$_3$): 7.37–7.24 (12H, m), 6.97 (2H, t, J=8.5 Hz), 5.83 (1H, brs), 5.75 (1H, brs); $^{19}$F NMR Γ(CHCl$_3$): −116.2 (1F, s); m.p 193–194° C.

5: $^1$H NMR Γ(CHCl$_3$): 7.41–7.34 (1H, m), 7.29–7.23 (4H, m), 7.16 (1H, ddd, J=18.1, 8.1 and 1.2 Hz), 7.15 (1H, d, J=7.7 Hz), 7.05–6.97 (4H,m), 6.93–6.87 (1H, dt, J=8.0 and 1.4 Hz), 5.90 (1H, brs), 5.74 (1H, brs); $^{19}$F NMR Γ(CHCl$_3$): −103.3 (1F, s), −115.5 (2F, s); m.p 168–169° C.

6 : $^1$H NMR Γ(CHCl$_3$): 7.64–7.54 (4H, m), 7.40–7.34 (6H, m), 5.70 (2H, brs); $^{19}$F NMR Γ(CHCl$_3$): 137.3 (2F, d, J=19.2 Hz), −155.8 (1F, t, J=21.4 Hz), −161.9 (2F, dd, J=21.4 and 17.1 Hz).

7: $^1$H NMR Γ(CHCl$_3$): 7.37–7.31 (6H, m), 7.28–7.20 (5H, m), 7.12–7.04 (2H, m), 5.90 ((1H, brs), 5.74 (1H, brs); $^{19}$F NMR Γ(CHCl$_3$): −137.8 to −137.9 (1F, m), −140.3 to −140.4 (1F, m); m.p 174–175° C.

8: $^1$H NMR Γ(CHCl$_3$): 7.37–7.28 (10H, m), 6.95–6.83 (2H, m), 6.81–6.75 (1H, m), 5.92 (1H, brs), 5.80 (H, brs); $^{19}$F NMR Γ(CHCl$_3$): −99.1 (1F, dd, J=19.2 and 8.5 Hz), −111.6 (1F, m); m.p 187–188° C.

9: $^1$H NMR Γ(CHCl$_3$): 7.38–7.22 (7H, m), 7.09–6.96 (6H, m), 5.83 (1H, brs), 5.77 (1H, brs); $^{19}$F NMR Γ(CHCl$_3$): −112.6 (2F, dd, J=17.1 and 6.4 Hz); m.p 195–196° C.

13: $^1$H NMR Γ(CHCl$_3$): 7.26–7.19 (6H, dd, J=9.0 and 5.4 Hz), 7.20–7.01 (6H, t, J=8.7 Hz), 5.83 (1H, brs), 5.69 (1H, brs); $^{19}$F NMR Γ(CHCl$_3$): −115.3 (3F, s); m.p 180–181° C.

14: $^1$H NMR Γ(CHCl$_3$): 7.39–7.27 (9H, m), 7.17–7.03 (4H, m), 5.90 (1H, brs), 5.85 (1H, brs); $^{19}$F NMR Γ(CHCl$_3$): −102.9 (2F, s); m.p 166–167° C.

15: $^1$H NMR Γ(CHCl$_3$): 7.41–7.34 (2H, m), 7.29–7.23 (4H, m), 7.17–7.05 (4H, m), 6.99 (2H, t, J=8.7 Hz), 5.78(2H, brs); $^{19}$F NMR Γ(CHCl$_3$): −103.0 (2F, s), −115.9 (1F, m); m.p 187–188° C.

16: $^1$H NMR Γ(CHCl$_3$): 7.34–7.20 (6H, m), 7.06–6.97 (6H, m), 5.90 (1H, brs), 5.71 (1H, brs); $^{19}$F NMR Γ(CHCl$_3$): −112.2 (1F, dd, J=17.1 and 7.4 Hz), −115.1 to −115.2 (2F, m); m.p 165–166° C.

17: $^1$H NMR Γ(CHCl$_3$): 7.35 –7.21 (3H, m), 7.06–6.97 (9H, m), 7.17–7.05 (4H, m), 5.96 (1H, brs), 5.76 (1H, brs); $^{19}$F NMR Γ(CHCl$_3$): −112.2 (3F, dd, J=17.1 and 8.5 Hz); m.p 186–188° C.

Example 2

This Example illustrates the assay of the compounds of the invention for their resistance to degradation in a biological medium. In this Example, human liver microsomes form the biological medium. The compounds of the invention were found to display a remarkable resistance to degradation by the microsome preparation, relative to non-fluorinated triphenylmethyl compounds.

2.1 Materials and Methods

Seventeen fluorinated triarylmethane compounds, clotrimazole, and a chlorinated triarylmethane compound 18 were tested for metabolic stability in vitro in a reaction mixture of human liver microsomes. The reaction mixture contained 1.0 mg/ml human liver microsomal protein, 100 mM potassium phosphate (pH 7.4), 10 mM MgCl$_2$ and an NADPH-generating system. The compounds were tested at a concentration of 5ΓM at 37° C. and the amount of intact compound remaining in the mixture after two hours calculated in terms of percent of original dose remaining.

2.2 Results

The results of this study demonstrate that the fluorinated compounds of the invention have an enhanced resistance towards degradation in a biological milieu than analogous non-fluorinated compounds. The results are collected in Table 2, above.

Example 3

This Example illustrates a pharmacokinetic study of the compounds of the invention in the rat. The fluorinated compounds of the invention were found to exhibit an in vivo half-life that was enhanced relative to non-fluorinated derivatives.

3.1 Materials and Methods

Pharmacokinetic studies were conducted in rats to extend the finding that selected fluoro substitution of the phenyl rings increased metabolic stability in vitro to an in vivo study. Compound 1, compound 3 and compound 18 were administered to groups of three to five male, Sprague-Dawley rats at doses of 1 mg/kg i.v. and 10 mg/kg p.o. to determine T$_{1/2}$ and oral bioavailability. Blood samples were collected at 9 time points from predosing to 24 hours after dosing p.o. and at 11 time points from pre-dosing to 24 hours after i.v. dosing. Samples were prepared and analyzed for compound plasma concentration using LC-MS/MS.

3.2 Results

As predicted from the in vitro metabolism data, compound 18 had very poor oral bioavailability with only very low levels (31 to 65 ng/mL) appearing in plasma between 0.25 and 1 hour after dosing and displaying no detectable levels by the 2 hour post-dose sample. By the i.v. route, the elimination from the bloodstream was fast. Because plasma levels were so low in the post-oral dosing samples, the percent bioavailability could not be calculated for compound 18.

In marked contrast to the results obtained with compound 18, compound 1 had much better oral bioavailability, 35%, and the oral availability for compound 3 was calculated to be 100%

The results of this pharmacokinetic experiment are displayed graphically in FIG. 1.

Example 4

Example 4 describes a bioassay for measuring the inhibition of a calcium activated potassium channel, the Gardos channel, in red blood cells by the compounds of the invention.

4.1 Materials and Methods

Heparinized whole blood was washed three times with Modified Flux Buffer (MFB: 140 mM NaCl; 5 mM KCl; 10 mM Tris; 0.1 mM EGTA; pH=7.4). Washed cells were then incubated for 3 hours with $^{86}$Rb (5 μCi/mL). After this incubation period, the RBCs were washed three times with cold MFB. Washed $^{86}$Rb loaded RBCs were then incubated with a test compound of the invention for 10 minutes. $^{86}$Rb flux was then initiated by the addition of 20 μL/mL of a MFB solution containing 10 mM CaCl$_2$ and 100 μM A23187, a calcium ionophore. This yielded a final concentration of 200 μM CaCl$_2$ and 2 μM A23187 n the incubation medium. Cells were incubated for 10 minutes, spun down and the supernatant was removed. Samples were counted in a Wallace Microbeta liquid scintillation counter by Cerenkov emission. Total RBC $^{86}$Rb content was determined by lysing the RBCs with water and then precipitating protein using a 50:50 mixture of ethanol:chloroform. After a 20 minute microfuge spin, the aqueous and organic layers separated and the aqueous layer was removed and counted. Efflux is expressed as a percentage of the initial cell content of $^{86}$Rb.

4.2 Results

The above-described bioassay demonstrated that the compounds of the invention are excellent inhibitors of the Gardos channel. Numeric results for the inhibition studies are displayed in Table 2, supra.

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

What is claimed is:

1. A compound having the structure:

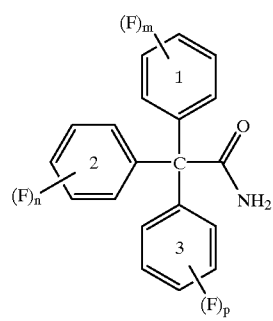

(I)

wherein,

- m, n and p are independently selected from 0 and 1 and at least one of m, n and p is 1;
- when m, n and p are all 1, the fluoro substituents at ring 1 and at ring 2 are located at a position independently selected from ortho to the acetamide substituent, meta to the acetamide substituent and para to the acetamide substituent, and the substituent at ring 3 is at a position selected from ortho to the acetamide substituent para to the acetamide substituent; and
- when p is 0, and m is 1 and n is 1, the fluoro substituent at ring 1 is para to the acetamide substituent, and the substituent at ring 2 is located at a position selected from ortho to the acetamide substituent and para to the acetamide substituent.

2. A compound according to claim 1 having the structure:

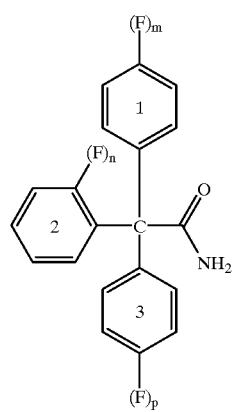

(II)

wherein, m, n and p are independently selected from 0 and 1, and at least one of m, n and p is 1.

3. A compound according to claim 2, having the structure:

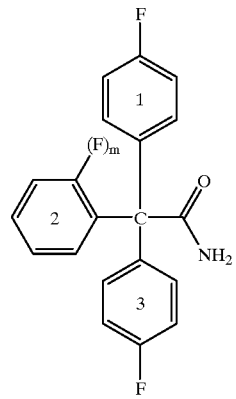

(III)

wherein m is either 0 or 1.

4. A compound according to claim 1, having a structure that is selected from:

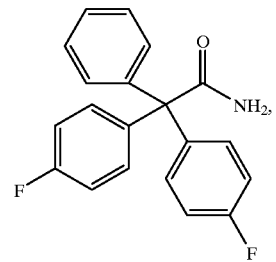

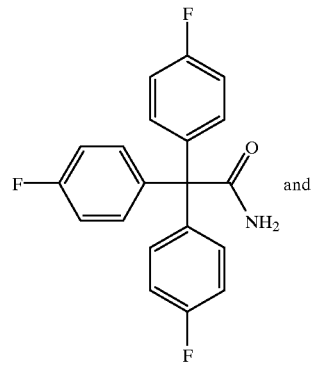

and

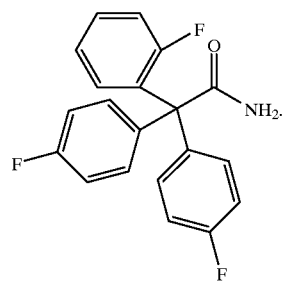

5. A pharmaceutical composition comprising a compound in admixture with a pharmaceutically acceptable excipient, said compound having the structure:

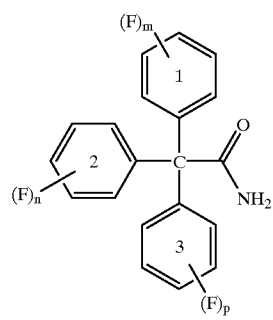

(I)

wherein, m, n and p are independently selected from 0 and 1 and at least one of m, n and p is 1;

when m, n and p are all 1, the fluoro substituents at ring 1 and at ring 2 are located at a position independently selected from ortho to the acetamide substituent, meta to the acetamide substituent and para to the acetamide substituent, and the substituent at ring 3 is at a position selected from ortho to the acetamide substituent para to the acetamide substituent; and when p is 0, and m is 1 and n is 1, the fluoro substituent at ring 1 is para to the acetamide substituent, and the substituent at ring 2 is located at a position selected from ortho to the acetamide substituent and para to the acetamide sub stituent.

6. The pharmaceutical formulation according to claim 5, said compound having the structure:

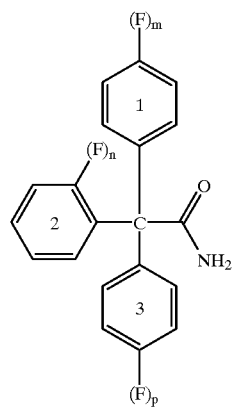

(II)

wherein, m, n and p are independently selected from 0 and 1, and at least one of m, n and p is 1.

7. The pharmaceutical formulation according to claim 6, said compound having the structure:

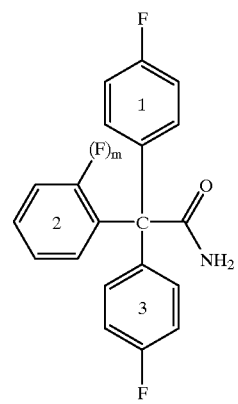

(III)

wherein m is either 0 or 1.

8. The pharmaceutical composition according to claim 5, said compound having a structure selected from:

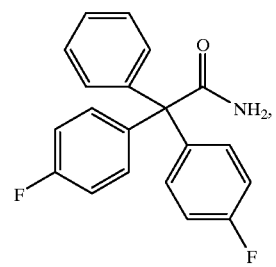

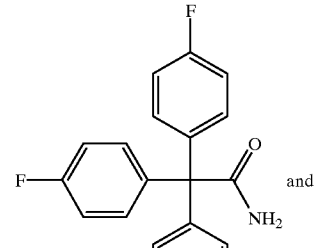
and

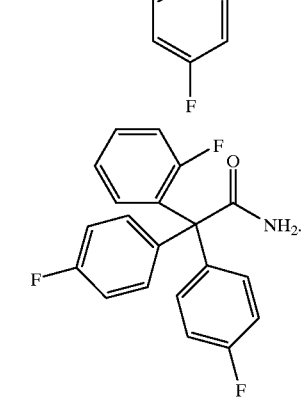

9. A method of inhibiting potassium flux of a cell, said method comprising contacting said cell with an effective amount of a compound having the structure:

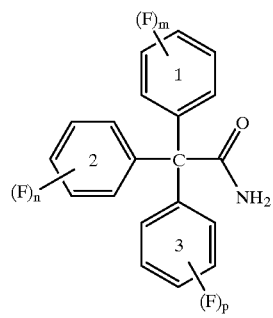

(I)

wherein, m, n and p are independently selected from 0 and 1 and at least one of m, n and p is 1;

when m, n and p are all 1, the fluoro substituents at ring 1 and at ring 2 are located at a position independently selected from ortho to the acetamide substituent, meta to the acetamide substituent and para to the acetamide substituent, and the substituent at ring 3 is at a position selected from ortho to the acetamide substituent para to the acetamide substituent; and when p is 0, and m is 1 and n is 1, the fluoro substituent at ring 1 is para to the acetamide substituent, and the substituent at ring 2 is located at a position selected from ortho to the acetamide substituent and para to the acetamide substituent.

10. The method according to claim 9, wherein said compound has the structure:

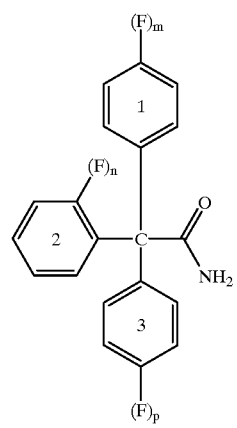

(II)

wherein, m, n and p are independently selected from 0 and 1, and at least one of m, n and p is 1.

11. The method according to claim 8, said compound having the structure:

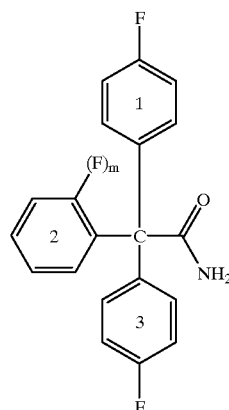

(III)

wherein m is either 0 or 1.

12. The method according to claim 9, said compound having a structure selected from:

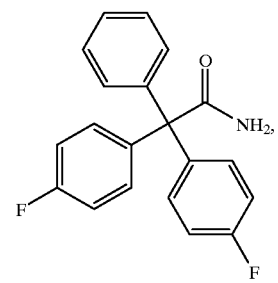

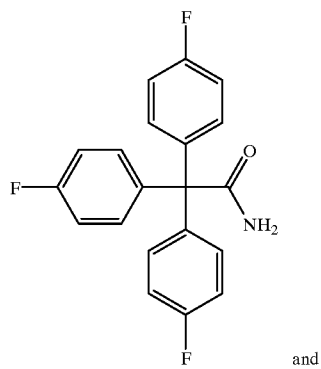

and

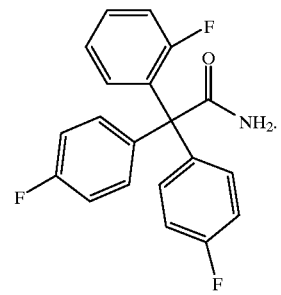

13. The method of claim 9, wherein said cell is an erythrocyte.

14. A method for reducing erythrocyte dehydration, said method comprising contacting said erythrocyte with an amount of a compound effective to reduce said dehydration, said compound having the structure:

(I)

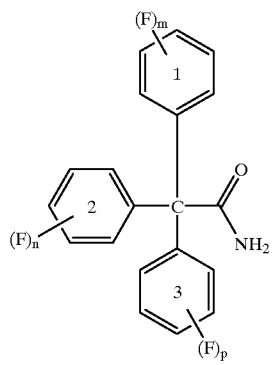

wherein, m, n and p are independently selected from 0 and 1 and at least one of m, n and p is 1;

when m, n and p are all 1, the fluoro substituents at ring 1 and at ring 2 are located at a position independently selected from ortho to the acetamide substituent, meta to the acetamide substituent and para to the acetamide substituent, and the substituent at ring 3 is at a position selected from ortho to the acetamide substituent para to the acetamide substituent; and when p is 0, and m is 1 and n is 1, the fluoro substituent at ring 1 is para to the acetamide substituent, and the substituent at ring 2 is located at a position selected from ortho to the acetamide substituent and para to the acetamide substituent.

15. The method according to claim 14, said compound having the structure:

(II)

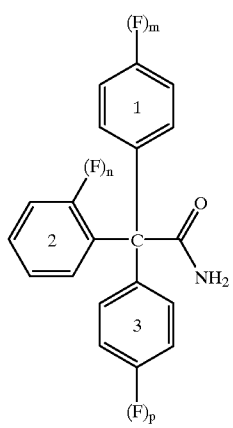

wherein, m, n and p are independently selected from 0 and 1, and at least one of m, n and p is 1.

16. The method according to claim 15, said compound having the structure:

(III)

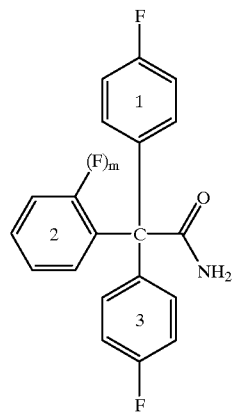

wherein m is either 0 or 1.

17. The method according to claim 14, said compound having a structure that is selected from:

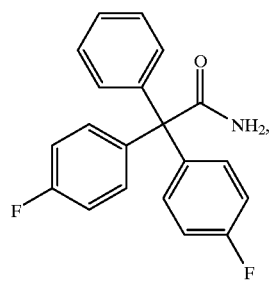

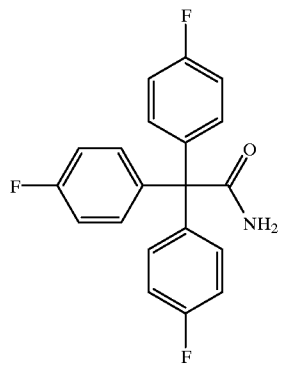

and

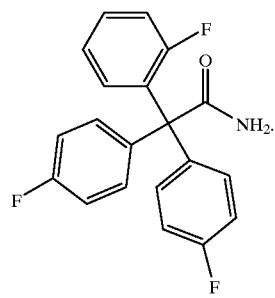

18. A method for treating or preventing a sickle cell disease event, said method comprising administering to a subject suffering sickle cell disease a therapeutically effective amount of a compound having the structure:

(I)

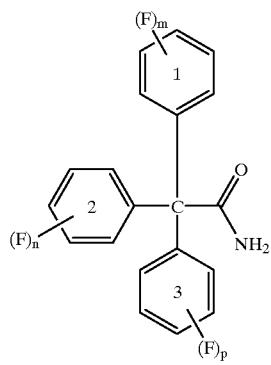

wherein, m, n and p are independently selected from 0 and 1 and at least one of m, n and p is 1;

when m, n and p are all 1, the fluoro substituents at ring 1 and at ring 2 are located at a position independently selected from ortho to the acetamide substituent, meta to the acetamide substituent and para to the acetamide substituent, and the substituent at ring 3 is at a position selected from ortho to the acetamide substituent para to the acetamide substituent; and when p is 0, and m is 1 and n is 1, the fluoro substituent at ring 1 is para to the acetamide substituent, and the substituent at ring 2 is located at a position selected from ortho to the acetamide substituent and para to the acetamide substituent.

19. The method according to claim 18, said compound having the structure:

(II)

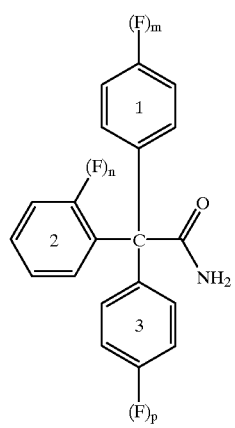

wherein, m, n and p are independently selected from 0 and 1, and at least one of m, n and p is 1.

20. The method according to claim 19, said compound having the structure:

(III)

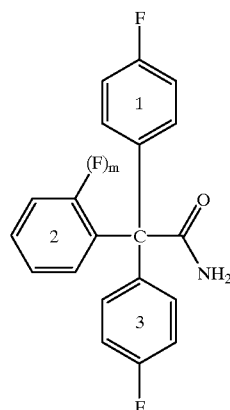

wherein m is either 0 or 1.

21. The method according to claim 18, said compound having a structure that is selected from:

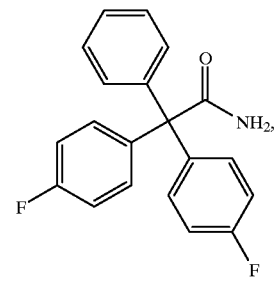

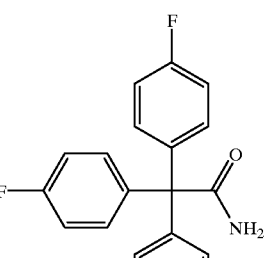

and

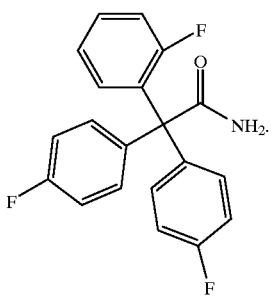

22. A method for enhancing resistance to degradation in a biological medium of a potassium channel inhibitor comprising a phenyl moiety, said method comprising, substituting a radical comprising a fluorine atom for a hydrogen atom on the aryl radical of the inhibitor.

23. The method of claim 22, wherein said potassium channel is IK1.

24. The method of claim 23, wherein said potassium channel is Gardos channel.

25. The method of claim 22, wherein said aryl radical is a component of a triarylmethyl radical.

* * * * *

UNITED STATES PATENT AND TRADEMARK OFFICE
CERTIFICATE OF CORRECTION

PATENT NO. : 6,288,122 B1
DATED : September 11, 2001
INVENTOR(S) : Grant Andrew McNaughton-Smith et al.

It is certified that error appears in the above-identified patent and that said Letters Patent is hereby corrected as shown below:

<u>Column 5,</u>
Line 24, delete "substituent para" and insert therefore -- substituent and para --;

<u>Column 7,</u>
Line 42, delete "substituent para" and insert therefore -- substituent and para --.

<u>Column 31,</u>
Line 35, delete "substituent para" and insert therefore -- substituent and para --;

<u>Column 32,</u>
Claim 3, in the formula, please delete the variable "(F)m" on Ring 2, and insert therefore -- (F)n --;

<u>Column 33,</u>
Line 29, delete "substituent para" and insert therefore -- substituent and para --;
Line 36, delete "sub stituent" and insert therefore -- substituent --;

<u>Column 34,</u>
Claim 7, in the formula, please delete the variable "(F)m" on Ring 2, and insert therefore -- (F)n --;

<u>Column 35,</u>
Line 29, delete "substituent para" and insert therefore -- substituent and para --;
Line 66, delete "claim 8" and insert therefore -- claim 9 --;

<u>Column 36,</u>
Claim 11, in the formula, please delete the variable "(F)m" on Ring 2, and insert therefore -- (F)n --;

<u>Column 37,</u>
Line 30, delete "substituent para" and insert therefore -- substituent and para --;

<u>Column 38,</u>
Claim 16, in the formula, please delete the variable "(F)m" on Ring 2, and insert therefore -- (F)n --;

<u>Column 39,</u>
Line 30, delete "substituent para" and insert therefore -- substituent and para --; and

UNITED STATES PATENT AND TRADEMARK OFFICE
CERTIFICATE OF CORRECTION

PATENT NO. : 6,288,122 B1
DATED : September 11, 2001
INVENTOR(S) : Grant Andrew McNaughton-Smith et al.

It is certified that error appears in the above-identified patent and that said Letters Patent is hereby corrected as shown below:

Column 40,
Claim 20, in the formula, please delete the variable "(F)m" on Ring 2, and insert therefore -- (F)n --.

Signed and Sealed this

Twenty-second Day of July, 2003

JAMES E. ROGAN
*Director of the United States Patent and Trademark Office*